(12) United States Patent
Zhou et al.

(10) Patent No.: US 12,054,630 B2
(45) Date of Patent: Aug. 6, 2024

(54) MODIFIED CARDANOL AS THE REACTIVE DILUENTS FOR ALKYD COATING

(71) Applicants: Qixin Zhou, Cuyahoga Falls, OH (US); Haoran Wang, Akron, OH (US)

(72) Inventors: Qixin Zhou, Cuyahoga Falls, OH (US); Haoran Wang, Akron, OH (US)

(73) Assignee: The University of Akron, Akron, OH (US)

( * ) Notice: Subject to any disclaimer, the term of this patent is extended or adjusted under 35 U.S.C. 154(b) by 625 days.

(21) Appl. No.: 16/791,306

(22) Filed: Feb. 14, 2020

(65) Prior Publication Data

US 2020/0263054 A1 Aug. 20, 2020

Related U.S. Application Data

(60) Provisional application No. 62/805,571, filed on Feb. 14, 2019.

(51) Int. Cl.
| | | |
|---|---|---|
| *C09D 167/08* | (2006.01) | |
| *C07C 69/54* | (2006.01) | |
| *C07F 7/18* | (2006.01) | |
| *C09D 4/06* | (2006.01) | |
| *C09D 5/08* | (2006.01) | |
| *C09D 7/20* | (2018.01) | |
| *C08K 3/32* | (2006.01) | |

(52) U.S. Cl.
CPC ............ *C09D 167/08* (2013.01); *C07C 69/54* (2013.01); *C07F 7/1804* (2013.01); *C09D 4/06* (2013.01); *C09D 5/084* (2013.01); *C09D 7/20* (2018.01); *C08K 2003/328* (2013.01)

(58) Field of Classification Search
CPC .......... C09D 167/08; C09D 7/20; C09D 4/06; C09D 5/084; C07C 69/54; C07F 7/1804; C08K 2003/328
See application file for complete search history.

(56) References Cited

U.S. PATENT DOCUMENTS

| | | |
|---|---|---|
| 4,097,677 A | 6/1978 | Emmons et al. |
| 4,387,190 A | 6/1983 | Feely |

(Continued)

FOREIGN PATENT DOCUMENTS

| | | |
|---|---|---|
| WO | 9702230 | 1/1997 |
| WO | 9800387 | 1/1998 |

OTHER PUBLICATIONS

John et al. "Cardanyl Acrylate/Methacrylate Based Cross-Linked Copolymers as Novel Supports: Synthesis and Characterization" Journal of Applied Polymer Science vol. 53, Issue 11, 1415-1423, 1994.*

(Continued)

*Primary Examiner* — Robert S Walters, Jr.
(74) *Attorney, Agent, or Firm* — Renner, Kenner, Greive, Bobak, Taylor & Weber

(57) ABSTRACT

A coating composition comprising at least one alkyd resin and at least one reactive diluent selected from modified cardanol. Optionally, the coating composition may further include at least one dryer agent, at least one pigment, and at least one solvent. The use of a modified cardanol reactive diluent can reduce the amount of volatile organic solvent, while decreasing drying time, increasing adhesion, and improving corrosion resistance.

13 Claims, 11 Drawing Sheets
(10 of 11 Drawing Sheet(s) Filed in Color)

(56) References Cited

U.S. PATENT DOCUMENTS

| | | | |
|---|---|---|---|
| 4,477,543 | A | 10/1984 | Bjorklund |
| 4,798,859 | A | 1/1989 | Hohlein et al. |
| 5,252,648 | A | 10/1993 | Hohlein et al. |
| 8,124,688 | B2 | 2/2012 | Meijer et al. |
| 8,987,370 | B2 | 3/2015 | Soucek et al. |
| 2007/0060713 | A1 | 3/2007 | Gracey et al. |

OTHER PUBLICATIONS

Gimeno et al. "Improvement of the anticorrosive properties of an alkyd coating with zinc phosphate pigments assessed by NSS and ACET" Progress in Organic Coatings vol. 95, 46-53, 2016.*

W. Araujo, I. Margarit, O. Mattos, F. Fragata, P. de Lima-Neto, Corrosion aspects of alkyd paints modified with linseed and soy oils, Electrochimica Acta, 55 (2010) 6204-6211.

F. Cadena, L. Irusta, M. Fernandez-Berridi, Performance evaluation of alkyd coatings for corrosion protection in urban and industrial environments, Progress in Organic Coatings, 76 (2013) 1273-1278.

B. Chico, J. Simancas, J. Vega, N. Granizo, I. Diaz, D. De La Fuente, M. Morcillo, Anticorrosive behaviour of alkyd paints formulated with ion-exchange pigments, Progress in Organic Coatings, 61 (2008) 283-290.

B. Del Amo, R. Romagnoli, V. Vetere, Steel corrosion protection by means of alkyd paints pigmented with calcium acid phosphate, Industrial & engineering chemistry research, 38 (1999) 2310-2314.

M. Deyab, Effect of carbon nano-tubes on the corrosion resistance of alkyd coating immersed in sodium chloride solution, Progress in Organic Coatings, 85 (2015) 146-150.

L. Ecco, M. Fedel, A. Ahniyaz, F. Deflorian, Influence of polyaniline and cerium oxide nanoparticles on the corrosion protection properties of alkyd coating, Progress in Organic Coatings, 77 (2014) 2031-2038.

C. Gervasi, A. Di Sarli, E. Cavalcanti, O. Ferraz, E. Bucharsky, S. Real, J. Vilche, The corrosion protection of steel in sea water using zinc-rich alkyd paints. An assessment of the pigment-content effect by EIS, Corrosion Science, 36 (1994) 1963-1972.

S. Gonzalez, I.M. Rosca, R. Souto, Investigation of the corrosion resistance characteristics of pigments in alkyd coatings on steel, Progress in Organic coatings, 43 (2001) 282-285.

J. Li, L. Ecco, M. Fedel, V. Ermini, G. Delmas, J. Pan, In-situ AFM and EIS study of a solventborne alkyd coating with hanoclay for corrosion protection of carbon steel, Progress in Organic Coatings, 87 (2015) 179-188.

B. Liu, Y. Li, H. Lin, C.-n. Cao, Effect of PVC on the diffusion behaviour of water through alkyd coatings, Corrosion Science, 44 (2002) 2657-2664.

J. Marsh, J. Scantlebury, S. Lyon, The effect of surface/primer treatments on the performance of alkyd coated steel, Corrosion science, 43 (2001) 829-852.

M. Marti, G. Fabregat, D.S. Azambuja, C. Aleman, E. Armelin, Evaluation of an environmentally friendly anticorrosive pigment for alkyd primer, Progress in Organic Coatings, 73 (2012) 321-329.

P.A. Sørensen, S. Kiil, K. Dam-Johansen, C.E. Weinell, Anticorrosive coatings: a review, Journal of Coatings Technology and Research, 6 (2009) 135-176.

A.H. Alidedeoglu, K. Davis, R. Robertson, C. Smith, J.W. Rawlins, S.E. Morgan, Synthesis and evaluation of tetra (2,7-octadienyl) titanate as a reactive diluent for air-drying alkyd paints, Journal of Coatings Technology and Research, 8 (2011) 45-52.

M. Irfan, S.I. Bhat, S. Ahmad, Reduced Graphene Oxide Reinforced Waterborne Soy Alkyd Nanocomposites: Formulation, Characterization, and Corrosion Inhibition Analysis, ACS Sustainable Chemistry & Engineering, 6 (2018) 14820-14830.

W. Muizebelt, J. Hubert, M. Nielen, R. Klaasen, K. Zabel, Crosslink mechanisms of high-solids alkyd resins in the presence of reactive diluents, Progress in Organic Coatings, 40 (2000) 121-130.

S. Pathan, S. Ahmad, Synergistic effects of linseed oil based waterborne alkyd and 3-isocynatopropyl triethoxysilane: Highly Transparent, Mechanically robust, thermally stable, hydrophobic, anticorrosive coatings, ACS Sustainable Chemistry & Engineering, 4 (2016) 3062-3075.

A. Popadyuk, A. Breuer, J. Bahr, I. Tarnavchyk, A. Voronov, B.J. Chisholm, Sucrose octaesters as reactive diluents for alkyd coatings, Journal of Coatings Technology and Research, 15 (2018) 481-488.

K. Zabel, R. Klaasen, W. Muizebelt, B. Gracey, C. Hallett, C. Brooks, Design and incorporation of reactive diluents for air-drying high solids alkyd paints, Progress in organic coatings, 35 (1999) 255-264.

C. Zhang, H. Wang, W. Zeng, Q. Zhou, High Biobased Carbon Content Polyurethane Dispersions Synthesized from Fatty Acid-Based Isocyanate, Industrial & Engineering Chemistry Research, 58 (2019) 5195-5201.

F.N. Jones, M.E. Nichols, S.P. Pappas, Organic coatings: science and technology, John Wiley & Sons, 2017.

P.P. Nalawade, B. Mehta, C. Pugh, M.D. Soucek, Modified soybean oil as a reactive diluent: Synthesis and characterization, Journal of Polymer Science Part A: Polymer Chemistry, 52 (2014) 3045-3059.

P.P. Nalawade, M.D. Soucek, Modified soybean oil as a reactive diluent: coating performance, Journal of Coatings Technology and Research, 12 (2015) 1005-1021.

F.N. Waitara, Evaluation of Cashew Nut Shell Liquid Based Products as Reactive Diluents for Alkyd Coatings, 2015.

K. Wutticharoenwong, J. Dziczkowski, M.D. Soucek, Tung based reactive diluents for alkyd systems: Film properties, Progress in Organic Coatings, 73 (2012) 283-290.

E. Calò, A. Maffezzoli, G. Mele, F. Martina, S.E. Mazzetto, A. Tarzia, C. Stifani, Synthesis of a novel cardanol-based benzoxazine monomer and environmentally sustainable production of polymers and bio-composites, Green Chemistry, 9 (2007) 754-759.

Y. Hu, Q. Shang, J. Tang, C. Wang, F. Zhang, P. Jia, G. Feng, Q. Wu, C. Liu, L. Hu, Use of cardanol-based acrylate as reactive diluent in UV-curable castor oil-based polyurethane acrylate resins, Industrial crops and products, 117 (2018) 295-302.

Y. Hu, Q. Shang, C. Wang, G. Feng, C. Liu, F. Xu, Y. Zhou, Renewable epoxidized cardanol-based acrylate as a reactive diluent for UV-curable resins, Polymers for Advanced Technologies, 29 (2018) 1852-1860.

G. John, C. Pillai, Synthesis and characterization of a self-crosslinkable polymer from cardanol: Autooxidation of poly (cardanyl acrylate) to crosslinked film, Journal of Polymer Science Part A: Polymer Chemistry, 31 (1993) 1069-1073.

G. John, C.K.S. Pillai, Self-crosslinkable monomer from cardanol: crosslinked beads of poly (cardanyl acrylate) by suspension polymerization, Die Makromolekulare Chemie, Rapid Communications, 13 (1992) 255-259.

R. Liu, X. Zhang, J. Zhu, X. Liu, Z. Wang, J. Yan, UV-curable coatings from multiarmed cardanol-based acrylate bligomers, ACS Sustainable Chemistry & Engineering, 3 (2015) 1313-1320.

C. Voirin, S. Caillol, N.V. Sadavarte, B.V. Tawade, B. Boutevin, P.P. Wadgaonkar, Functionalization of cardanol: towards biobased polymers and additives, Polymer Chemistry, 5 (2014) 3142-3162.

H. Wang, Q. Zhou, Synthesis of Cardanol-Based Polyols via Thiol-ene/Thiol-epoxy Dual Click-Reactions and Thermosetting Polyurethanes Therefrom, ACS Sustainable Chemistry & Engineering, 6 (2018) 12088-12095.

H. Wang, C. Zhang, W. Zeng, Q. Zhou, Making alkyd greener: Modified cardanol as bio-based reactive diluents for alkyd coating, Progress in Organic Coatings, 135 (2019) 281-290.

M. Attar, Investigation on zinc phosphate effectiveness at different pigment volume concentrations via electrochemical impedance spectroscopy, Electrochimica Acta, 50 (2005) 4645-4648.

Y. Hao, F. Liu, E.-H. Han, S. Anjum, G. Xu, The mechanism of inhibition by zinc phosphate in an epoxy coating, Corrosion Science, 69 (2013) 77-86.

Y. Shao, C. Jia, G. Meng, T. Zhang, F. Wang, The role of a zinc phosphate pigment in the corrosion of scratched epoxy-coated steel, Corrosion Science, 51 (2009) 371-379.

R. Salata, B. Pellegrene, M. Soucek, Migration of fluorinated alkyd and fluorinated tung oil additives for partially self-stratifying coatings, Progress in Organic Coatings, 133 (2019) 406-417.

(56) References Cited

OTHER PUBLICATIONS

R.R. Salata, B. Pellegrene, M.D. Soucek, Synthesis and properties of a high solids triethoxysilane-modified alkyd coatings, Progress in Organic Coatings, 133 (2019) 340-349.

K. Wutticharoenwong, M.D. Soucek, Synthesis of Tung-Oil-Based Reactive Diluents, Macromolecular Materials and Engineering, 295 (2010) 1097-1106.

M. Soucek, T. Khattab, J. Wu, Review of autoxidation and driers, Progress in Organic Coatings, 73 (2012) 435-454.

J. Honzíček, Curing of Air-Drying Paints: A Critical Review, Industrial & Engineering Chemistry Research, 58 (2019) 12485-12505.

S. Erich, J. Laven, L. Pel, H. Huinink, K. Kopinga, Dynamics of cross linking fronts in alkyd coatings, Applied Physics Letters, 86 (2005) 134105.

B. Marton, L.G. van der Ven, C. Otto, N. Uzunbajakava, M.A. Hempenius, G.J. Vancso, A depth-resolved look at the network development in alkyd coatings by confocal Raman microspectroscopy, Polymer, 46 (2005) 11330-11339.

G. Mirone, B. Marton, G.J. Vancso, Elastic modulus profiles in the cross sections of drying alkyd coating films: modelling and experiments, European polymer journal, 40 (2004) 549-560.

H. Wang, Q. Zhou, Evaluation and failure analysis of linseed oil encapsulated self-healing anticorrosive coating, Progress in Organic Coatings, 118 (2018) 108-115.

C. Zhang, H. Wang, Q. Zhou, Preparation and characterization of microcapsules based self-healing coatings containing epoxy ester as healing agent, Progress in Organic Coatings, 125 (2018) 403-410.

G. Bierwagen, D. Tallman, J. Li, L. He, C. Jeffcoate, EIS studies of coated metals in accelerated exposure, Progress in Organic Coatings, 46 (2003) 149-158.

M. Hattori, A. Nishikata, T. Tsuru, EIS study on degradation of polymer-coated steel under ultraviolet radiation, Corrosion Science, 52 (2010) 2080-2087. [50] F. Mansfeld, C. Tsai, Determination of coating deterioration with EIS: I. Basic relationships, Corrosion, 47 (1991) 958-963.

F. Mansfeld, C. Tsai, Determination of coating deterioration with EIS: I. Basic relationships, Corrosion, 47 (1991) 958-963.

C. Tsai, F. Mansfeld, Determination of coating deterioration with EIS: Part II. Development of a method for field testing of protective coatings, Corrosion, 49 (1993) 726-737.

Y. He, Y. Boluk, J. Pan, A. Ahniyaz, T. Deltin, P.M. Claesson, Corrosion protective properties of cellulose nanocrystals reinforced waterborne acrylate-based composite coating, Corrosion Science, 155 (2019) 186-194.

B. Ramezanzadeh, G. Bahlakeh, M. Ramezanzadeh, Polyaniline-cerium oxide (PAni—CeO2) coated graphene oxide for enhancement of epoxy coating corrosion protection performance on mild steel, Corrosion Science, 137 (2018) 111-126.

C. Hsu, F. Mansfeld, Concerning the conversion of the constant phase element parameter Y0 into a capacitance, Corrosion, 57 (2001) 747-748.

J. Hu, J. Zhang, C. Cao, Determination of water uptake and diffusion of Cl-ion in epoxy primer on aluminum alloys in NaCl solution by electrochemical impedance spectroscopy, Progress in Organic Coatings, 46 (2003) 273-279.

M. Harun, J. Marsh, S. Lyon, The effect of surface modification on the cathodic disbondment rate of epoxy and alkyd coatings, Progress in organic coatings, 54 (2005) 317-321.

F.X. Perrin, M. Irigoyen, E. Aragon, J. Vernet, Artificial aging of acrylurethane and alkyd paints: a micro-ATR spectroscopic study, Polymer Degradation and Stability, 70 (2000) 469-475.

Alp H. Alidedeoglu, Kevin Davis, Rhonda Robertson, Crystal Smith, James W. Rawlins, Sarah E. Morgan, Synthesis and evaluation of tetra(2,7-octadienyl) titanate as a reactive diluent for air-drying alkyd paints, J. Coat. Technol. Res., 8 (1) 45-52, 2011.

Haoran Wang, Cheng Zhang, Weixiu Zeng, Qixin Zhou, Making alkyd greener: Modified cardanol as bio-based reactive diluents for alkyd coating, https://doi.org/10.1016/j.porgcoat.2019.06.018.

Andriy Popadyuk, Austin Breuer, James Bahr, Ihor Tarnavchyk, Andriy Voronov, Bret J. Chisholm, Sucrose octaesters as reactive diluents for alkyd coatings, J. Coat. Technol. Res., 15 (3) 481-488, 2018.

* cited by examiner

MODIFIED CARDANOL AS THE REACTIVE DILUENTS FOR ALKYD COATING

CROSS-REFERENCE TO RELATED APPLICATION

This application claims priority from U.S. provisional patent application Ser. No. 62/805,571 filed on Feb. 14, 2019, which is incorporated herein by reference in its entirety.

FIELD OF THE INVENTION

One or more embodiments of the invention provide alkyd coating compositions that include a reactive diluent based upon modified cardanol, including anti-corrosive coating compositions and method of coating substrates. In addition to coatings, the compositions of the present invention are useful as films, adhesives, and sealants.

BACKGROUND OF THE INVENTION

Due to the non-renewable feature of petroleum resources, there are increasing interests in developing and utilizing chemicals and materials from renewable bio-based resources. Alkyd is the most widely used bio-based polymer resin in the coating industry. Around one million metric tons of alkyd resin is consumed each year, and the consumption is believed to have an increasing trend driven by the growing demand for bio-based coatings. Alkyd is a polyester that is synthesized from dibasic acids, polyols, and naturally occurring drying oils. Due to its low surface tension feature and autoxidative curing mechanism, alkyd coatings are usually characterized by excellent adhesion, few coating defects, and ease of application.

However, the presence of emulsifiers in the cured alkyd coatings generally leads to inferior water and corrosion resistance. In a traditional alkyd coating formulation, 30-60 wt. % volatile organic solvents are used to reduce the viscosity of the coating system to facilitate the application process. Due to the harmful effect of volatile organic compounds (VOCs) on the environment and human health, the development of high solid alkyd coating to reduce VOCs emissions is in growing demand. Over the past decades, waterborne alkyd coatings with low VOC content were developed with the aid of emulsifiers.

One effective approach to achieve high solid coating is using a reactive diluent. Reactive diluent is a chemical that can reduce the viscosity of the coating resin and react with the coating resin during the film formation process. The key properties of a reactive diluent for alkyd coating include low viscosity, compatibility with alkyd, low volatility, and the ability to participate in the autoxidative curing process.

A number of reactive diluents have been described in the literature.

U.S. Pat. No. 8,987,370 discloses the process for the preparation of tung oil-based reactive diluents for alkyd coating made by the Diels-Alder reaction.

U.S. Pat. No. 4,798,859 discloses the use of polyhdroxyl compounds containing ester and ether groups as the reactive diluents for alkyd coating.

U.S. Pat. No. 2007/0060713A1 discloses the process for the preparation of ether esters and allylic acetals which is suitable for use as the reactive diluents for alkyd coating.

International Patent Application Pub. No. WO 97/02230 discloses the use of 2-(2,7-octadienoxy) di(2,7-octadienyl) succinate as a reactive diluent in an alkyd coating formulation.

International Patent Application Pub. No. WO 98/00387 discloses the use of a composition comprising a mixture of a fumarate, maleate and 2-allyloxy-succinate esters as a reactive diluent in an alkyd coating formulation.

European Pat. No. EP 072127 discloses an alkyd resin system containing a reactive diluent selected from the group consisting of dicyclopentenyl methacrylate and dicyclopentenyloxy alkyl methacrylate.

U.S. Pat. No. 8,124,688 discloses the use of the ester of malonic and an unsaturated mono-alcohol as the reactive diluents for alkyd coating.

U.S. Pat. No. 5,252,648 discloses the use of octadienyl ethers as the reactive diluents for alkyd coating.

U.S. Pat. No. 4,097,677 discloses the use of the unsaturated esters of glycol monodicyclopentenyl ethers as the reactive diluents for alkyd coating.

U.S. Pat. No. 4,477,534 discloses the use of vinyl oxazoline esters as the reactive diluents for alkyd coating.

Alp H. Alidedeoglu et. al, "Synthesis and evaluation of tetra(2,7-octadienyl) titanate as a reactive diluent for air-drying alkyd paints", J. Coat. Technol. Res., 8 (1), 45-52 (2011) disclose the synthesis and application of tetra(2,7-octadienyl) titanate as a reactive diluent for air-drying alkyd paints.

Andriy Popadyuk et. al, "Sucrose octaesters as reactive diluents for alkyd coatings", J. Coat. Technol. Res., 15 (3), 481-488 (2018) disclose the use of sucrose octaesters as reactive diluents for alkyd coatings.

However, some of the current reactive diluents generate toxic volatiles as a side reaction of oxidative drying. Some lead to reduced gloss, extended drying times, and/or tacky surfaces. Corrosion resistance is also a concern.

Hence, it would be desirable to identify a reactive diluent to at least partially replace the organic solvent in alkyd coating formulations while overcoming the drawbacks mentioned above.

SUMMARY OF THE INVENTION

One or more embodiments of the present invention provide cardanol-based reactive diluents for alkyd coating applications. Methacrylated cardanol (MACO) and triethoxysilane-functionalized cardanol (TSCO) were designed and synthesized for application as the reactive diluents.

One or more embodiments of the present invention further provide alkyd coating compositions comprising at least one alkyd resin, at least one reactive diluent selected from modified cardanol, and optionally, at least one dryer agent, optionally, at least one pigment, and, optionally, at least one solvent.

One or more embodiments of the present invention further provide a cardanol-based reactive diluent for alkyd coating applications, wherein the diluent is selected from the group consisting of methacrylated cardanol and triethoxysilane-functionalized cardanol.

One or more embodiments of the present invention further provide a method for preparing cardanol-based reactive diluents.

One or more embodiments of the present invention further provide a method for preparing alkyd coating compositions.

One or more embodiments of the present invention further provide alkyd coatings for corrosion protection that include inhibitive pigments and that may be cured at room temperature.

One or more embodiments of the present invention further provide a zinc phosphate pigmented alkyd coating that is suitable for coating metal substrates.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
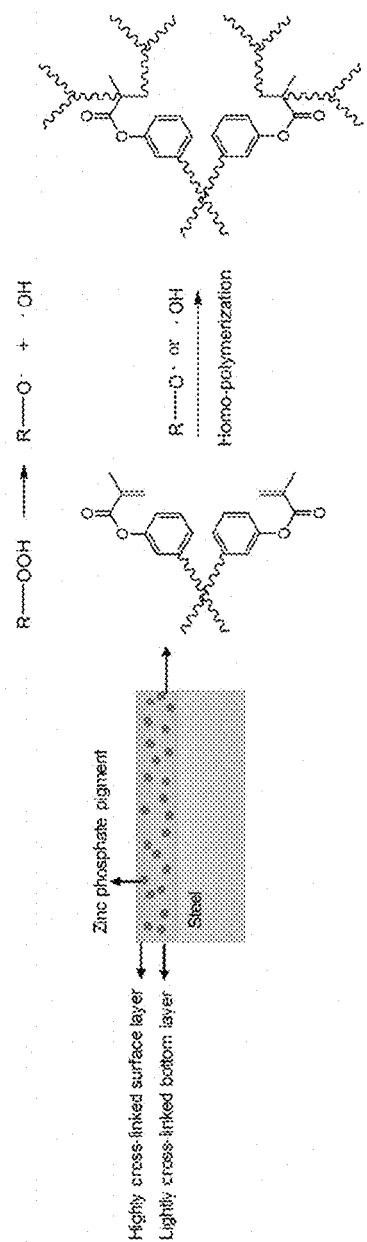
FIG. 1 is a schematic drawing that illustrates a free radical homo-polymerization induced cross-linking in the drying process of MACO modified alkyd coating.

One or more embodiments of this invention is based upon the discovery that modified cardanol is useful as a reactive diluent for alkyd coatings. While, for purposes of convenience, the compositions described herein are referred to as coating compositions, it should be understood that, in addition to coatings, the compositions of the present invention are useful as films, adhesives, and sealants.

In one or more embodiments, the present invention provides a coating composition that includes an alkyd resin and a reactive diluent. The composition may further include one or more of dryer agents, pigments, and additional solvents.

Alkyd Resin

Alkyds are sometimes described as polyesters that are modified by the addition of fatty acids and other components. An alkyd resin may be derived from polyols and a dicarboxylic acid or carboxylic acid anhydride.

Alkyd resins may be drying or nondrying. Drying alkyd resins are sometimes triglycerides that are derived from polyunsaturated fatty acids. In one or more embodiments, the triglycerides may be derived from plant or vegetable oils. Typical sources of drying oils for alkyd coatings include tung oil, linseed oil, sunflower oil, safflower oil, walnut oil, soybean oil, fish oil, corn oil, coconut oil, DCO (made by dehydrating castor oil, which creates a semi-drying, conjugated, oil/fatty acid), and tall oil (resinous oil by-product from pulp and paper manufacturing). In one or more embodiments, the alkyd resin is derived from linseed oil, soybean oil, or a combination thereof. In one or more embodiments, the alkyd resin may be used in combination with other resins, for example acrylic resins or polyurethanes.

In one or more embodiments, the number average molecular weight Mw of the alkyd resin is above 150 g/mol, in other embodiments, at least 300 g/mol, in other embodiments, at least 500 g/mol, in other embodiments, at least 1,000 g/mol, and in other embodiments, at least 5,000 g/mol. In one or more embodiments, the number average molecular weight Mw of the alkyd resin is below 120,000 g/mol, in other embodiments, less than 100,000 g/mol, in other embodiments, less than 80,000 g/mol.

In one or more embodiments, alkyd resins may be characterized by their oil length, where oil length is defined as the weight percentage of fatty acid building blocks (calculated as their triglycerides) in the alkyd resin. Long oil lengths (55% or higher) may contribute to improved oxidative drying, good substrate adhesion, excellent flow properties, good solubility in aliphatic solvents, and low viscosity, even with low solvent content. However, these alkyds show strong yellowing. Medium oil length alkyds (40-55%) may also have good solubility but may lead to a higher viscosity. Short oil length alkyds (less than 40%) may require additional measures, such as the use of additional siccatives or amino resins, to obtain acceptable drying times.

In one or more embodiments, the alkyd resin is characterized by an oil length of at least 40%, in other embodiments, at least 45%, in other embodiments, at least 50%, in other embodiments, at least 55%, in other embodiments, at least 60%.

In one or more embodiments, the alkyd resin may be prepared from soybean oil, glycerol, phthalic anhydride and lithium hydroxide. In one or more embodiments, the alkyd resin may be prepared from linseed oil, glycerol, phthalic anhydride and lithium hydroxide. In one or more embodiments, the alkyd resin is a mixture of compounds that may be represented by the formula:

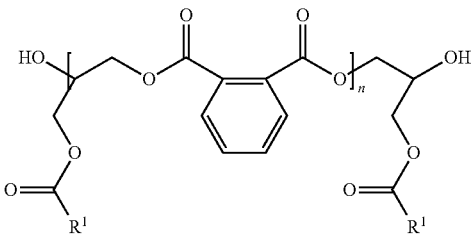

wherein $R^1$ is a $C_{17}$ hydrocarbon chain containing from zero to three double bonds, and where n is from about 1 to about 20.

In one or more embodiments, the alkyd includes the following distribution for $R^1$:

a

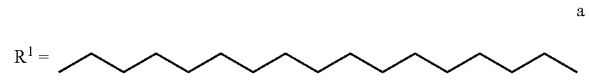

$R^1 =$

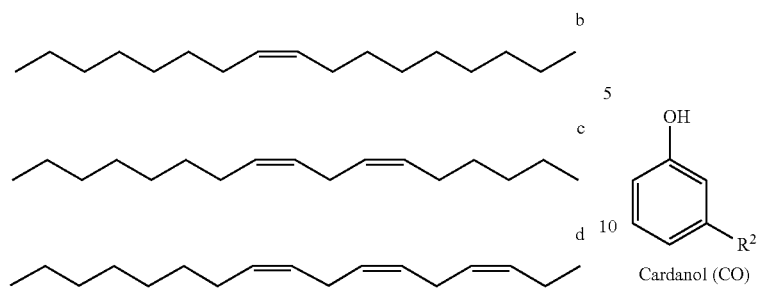

wherein a, b, c, and d are individually percentages of from 0 to about 100, based upon the total weight of the alkyd, wherein a+b+c+d=100, and wherein the average number of diallylic groups in $R^1$ is about 2.2 or greater.

In one or more embodiments, a is from about 0 to about 10, in other embodiments, from about 3 to about 7%. In one or more embodiments, b is from about 0 to about 60, in other embodiments, from about 5 to about 50, in other embodiments, about 40%. In one or more embodiments, c is from about 0 to about 80, in other embodiments, from about 5 to about 60, in other embodiments, from about 10 to about 50, in other embodiments, about 15%. In one or more embodiments, d is from about 0 to about 60, in other embodiments, from about 5 to about 50, in other embodiments, about 40%.

Generally, while the amount of alkyd resin in the coating composition is not necessarily limited, it may contribute to the viscosity of the coating composition. In one or more embodiments, the coating composition comprises at least 15 wt. % of alkyd resin, in other embodiments, at least 20 wt. %, and in other embodiments, at least 25 wt. % alkyd resin, based upon the total weight of the coating composition.

In one or more embodiments, the coating composition comprises no more than about 80 wt. % of alkyd resin, in other embodiments, no more than about 70 wt. %, in other embodiments, no more than about 50 wt. %, in other embodiments, no more than about 40 wt. %, and in other embodiments, no more than about 30 wt. % alkyd resin, based upon the total weight of the coating composition.

Reactive Diluent

In one or more embodiments, the reactive diluent is characterized by low viscosity, low volatility, compatibility with the alkyd, and the capability to participate in the oxidative cross-linking of the alkyd.

In one or more embodiments, the reactive diluent is a modified form of cardanol. Cardanol, sometimes abbreviated as CO, is a bio-based chemical derived from cashew nut shells. Advantageously, cardanol meets the above criteria, and is renewable. The alkyl phenolic structure of CO makes CO compatible with alkyd, and the diallylic methylene group in the side alkyl chain provides the ability of oxidative cross-linking. In one or more embodiments, CO is modified by functionalizing the CO at the phenolic hydroxyl group, as exemplified in Schemes 1 and 2 below. More specifically, in one or more embodiments, CO may be modified by reacting the phenolic hydroxyl group with an anhydride group (e.g., of methacrylic anhydride) via an esterification reaction (Scheme 1), or by reacting the phenolic hydroxyl group with an isocyanate group (e.g., of 3-isocyanatopropyl triethoxysilane) via an urethanization reaction (Scheme 2).

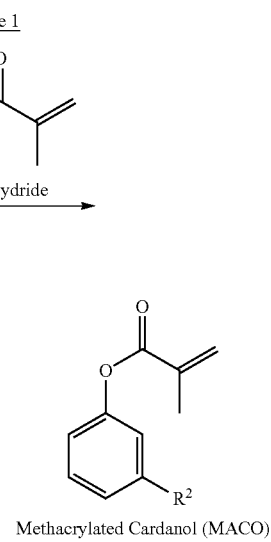

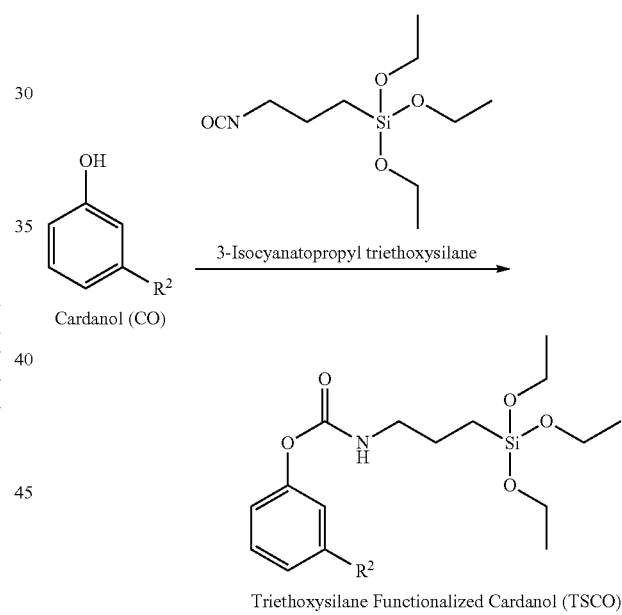

It has advantageously been found that properties such as hardness, adhesion, solvent resistance, and corrosion resistance of alkyd coatings can be improved by modifying CO to include one or more functional groups that are capable of oxidative cross-linking with the alkyd. Examples of these functional groups include methacrylate and alkoxysilane groups. When CO is modified to include a methacrylate group, the modified CO may be referred to as methacrylated cardanol (MACO). When CO is modified to include an alkoxysilane group, such as triethoxysilane, the modified CO may be referred to as triethoxysilane functionalized cardanol (TSCO).

In one or more embodiments, the modified CO is a mixture of compounds that may be represented by the following formula:

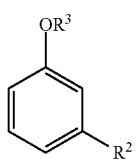

wherein $R^2$ is a $C_{15}$ hydrocarbon chain containing from zero to three double bonds, and wherein $R^3$ is a functional group that is capable of cross-linking. In one or more embodiments, the mixture of modified CO compounds has an average of about two double bonds in the $R^2$ group.

In one or more embodiments, the modified CO includes the following distribution for $R^2$:

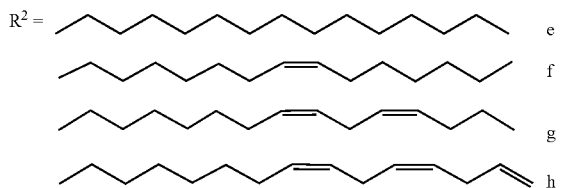

wherein e, f, g and h are individually percentages of from 0 to about 100, based upon the total weight of the modified cardanol, and wherein e+f+g+h=100.

In one or more embodiments, the modified CO may be represented by the following formula:

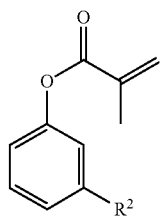

wherein $R^2$ is as described above.

In one or more embodiments, the modified CO may be represented by the following formula:

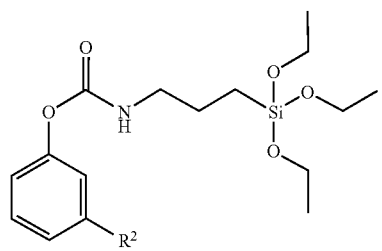

wherein $R^2$ is as described above.

In one or more embodiments, the reactive diluents according to the present invention are useful for thermally cured and/or room-temperature cured alkyd coatings. In these or other embodiments, the reactive diluents are useful for clear and/or pigmented alkyd coatings. In certain embodiments, the reactive diluents may be used with alkyds of any oil length.

In one or more embodiments, the coating compositions of the present invention include at least about 1 wt. % of reactive diluent, based upon the total weight of the coating composition, in other embodiments, at least about 5 wt. %, in other embodiments, at least about 10 wt. %, and in other embodiments, at least about 15 wt. %.

In one or more embodiments, the coating compositions of the present invention include from about 1 to about 40 wt. % of reactive diluent, based upon the total weight of the coating composition, in other embodiments, from about 5 to about 35 wt. %, and in other embodiments, from about 10 to about 20 wt. % reactive diluent, based upon the total weight of the coating composition.

Dryer Agent

In one or more embodiments, the coating compositions of the present invention include one or more siccatives, or dryer agents. Examples of siccatives include metal salts of aliphatic acids, including cycloaliphatic acids, or aromatic acids, such as ethylhexanoic acid, octanoic acid, and naphthenic acid, where the metal is, for example, cobalt, manganese, lead, vanadium, iron, zirconium, calcium, copper, potassium, lithium, zinc, aluminum, magnesium, bismuth, or a rare earth metal. Examples also include metal oxide acetylacetonates, metal acetyl-acetonates, metal chlorides, metal sulphates, and metal alcoholates, where the metal is, for example, selected from the above-mentioned metals. Mixtures of siccatives can also be used. In one or more embodiments, the siccatives (calculated as metal) are present in an amount of from about 0.001 to about 3 wt. %, based upon the total coating composition solids content.

In these or other embodiments, the coating composition may optionally comprise drying-accelerating complexing agents, for example, 2,2'-bipyridyl and 1,10-phenantroline. The complexing agents can be added in an amount of from about 0 to about 3 wt. %, in other embodiments, from about 0.1 to about 1.5 wt. %, based on the weight of the total coating composition.

In one or more embodiments, the siccative may support the formation of the coating via an oxidatively drying mechanism.

Pigment

The composition according to the invention can be used as a clear varnish or may contain pigments. Examples of pigments include opacifying pigments, tinting pigments, and filler pigments. Examples of opacifying pigments include titanium dioxide, zinc oxide, leaded zinc oxide, and titanium calcium. Tinting pigments include carbon black, yellow oxides, brown oxides, tan oxides, raw and burnt sienna or umber, chromium oxide green, phthalocyanine green, phthalonitrile blue, ultramarine blue, cadmium pigments and chromium pigments. Fillers include clay, silica, talc, mica, and the like. Combinations of pigment may also be used.

In one or more embodiments, the pigment is a corrosion-inhibitive pigment. Examples include calcium zinc phosphomolybdate, aluminum triphosphate, zinc phosphate, zinc iron phosphate, strontium zinc phosphosilicate, calcium phosphosilicate, zinc aluminum phosphate, lead-containing materials, and chromate-containing materials. Corrosion inhibitive pigments are further described in U.S. Pat. Nos. 7,481,877 and 9,840,625, both of which are incorporated herein by reference.

In one or more embodiments, the amount of pigment in the coating composition is from about 0 up to the critical pigment volume concentration (CPVC). CPVC is further described in U.S. Pat. No. 10,557,013, which is incorporated herein by reference. In one or more embodiments, the coating composition comprises from 5 to about 50 wt. % pigment, based upon the total weight of the coating composition.

Additional Solvent

In one or more embodiments, the coating composition is a solvent borne coating composition, and contains one or more solvents. In one or more embodiments, the solvent is an organic solvent. Examples of organic solvents include aromatic solvents such as toluene and xylene, as well as aliphatic solvents such as ethyl diglycol, ethyl glycol acetate, butyl glycol, butyl glycol acetate, butyl diglycol, butyl diglycol acetate, and methoxypropylene glycol acetate. As is known in the art, one or more of these solvents may be classified as volatile organic compounds, and may contribute to the volatile organic content (VOC) of the coating composition.

Advantageously, the reactive diluents of the present invention enable the reduction, or even elimination of the solvent, while maintaining or even improving the viscosity and/or other properties of the coating composition. In one or more embodiments, the amount of organic solvent is less than about 50 wt. %, in other embodiments, less than about 40 wt. %, in other embodiments, less than about 30 wt. %, and in other embodiments, less than about 20 wt. %, based upon the total weight of the coating composition.

In one or more embodiments, the volatile organic content (VOC) of coating compositions of the present invention is below 300 g/l. In this context, VOC is determined in accordance with US standard ASTM D 2369 (one hour at 110° C.).

In one or more embodiments, the coating compositions may be referred to as high solids compositions. In one or more embodiments, the solids content is at least 60%, in other embodiments, at least 70%, in other embodiments, at least 80%, and in other embodiments, at least 85% solids. In one or more embodiments, the solids content may be determined by combining the weight percentages of all ingredients other than the solvent.

The reactive diluents of the present invention may also be used in coating compositions with a higher solvent content.

In one or more embodiments, the reactive diluents may be formulated into air-drying waterborne compositions by combining them with alkyd emulsions, optionally comprising co-solvents or humectants, such as glycols. Waterborne coating systems are further described in U.S. Pat. No. 8,987,370, which is incorporated herein by reference.

The coating composition can furthermore contain one or more additives such as UV stabilizers, cosolvents, dispersants, surfactants, inhibitors, fillers, anti-static agents, flame-retardant agents, lubricants, anti-foaming agents, extenders, plasticizers, anti-freezing agents, waxes, thickeners, thixotropic agents, etc. Furthermore, the coating composition according to the invention may optionally comprise various anti-oxidants and anti-skinning agents.

Preparation of the Coating Composition.

In one or more embodiments, the coating composition may be prepared by combining the alkyd, reactive diluent, and other optional ingredients.

Formation of the Coating.

Compositions of the present invention may be used in forming films, paints, lacquers, varnishes, coatings, impregnates, and adhesives for both natural and synthetic materials, such as paper, textiles, wood, plastics, metal, and leather, as binders for non-woven fabrics, and in a wide variety of other uses.

In one or more embodiments, the coating composition may be cast onto a substrate to form a wet film, and then the film may be cured to form a coating. In one or more embodiments, the wet film may be thermally cured, and in other embodiments, the wet film may be cured at about room temperature as the film dries (air drying).

Advantageously, in one or more embodiments, the time for air drying of the wet film cast from a coating composition of the present invention is reduced, when compared to the same coating compositions but without reactive diluent. In one or more embodiments, the time for air drying of the wet film cast from a coating composition of the present invention is reduced by at least about 4 hours, when compared to the same coating compositions but without reactive diluent.

In one or more embodiments, the time for air drying of the wet film cast from a coating composition of the present invention is reduced, when compared to the same coating compositions but with the same amount of un-modified cardanol as the reactive diluent.

As illustrated in FIG. 1, the formation of the cured coating may include free-radical homopolymerization of the modified cardanol (particularly the methacrylate-modified cardanol), which may increase cross-linking density of the coating, mechanical strength, and decrease drying time.

In one or more embodiments, the wet film may be thermally cured. The step of thermal curing may be conducted at about 120° C. for about 2 hours. Optionally, the first step of thermal curing may be followed by a second step of thermally curing, which may, for example, be conducted at about 160° C. for about 3 hours.

In one or more embodiments, the thickness of the cured coating is from about 1 to about 100 micrometers (μm), in other embodiments, from about 35 to about 45 μm.

Advantages of the Coating.

Embodiments of the present invention provide a reactive diluent for pigmented alkyd coatings. In one or more embodiments, the reactive diluents of the present invention provide decreased drying time, increased pull-off adhesion strength, and/or improved corrosion resistance. In one or more embodiments, the reactive diluents of the present invention exhibit improved dilution efficiency for alkyds, when compared to unmodified cardanol.

Figure 2:
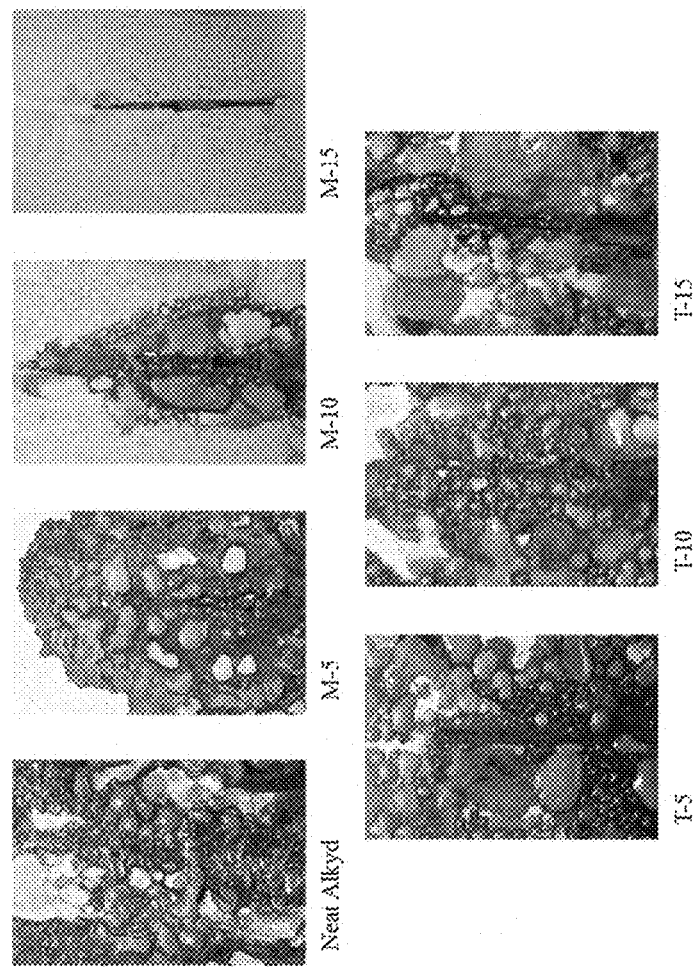
FIG. 2 shows the appearance of seven alkyd coatings, each after 480 hours of exposure in a salt fog chamber.

In one or more embodiments, zinc phosphate pigmented alkyd coating compositions containing MACO demonstrate improved corrosion resistance when compared to the same coating composition but without the MACO reactive diluent. For example, as shown in FIG. 2, the appearance of a MACO-containing alkyd coating was much improved over a neat alkyd coating after 480 hours of exposure in a fog chamber. In one or more embodiments, the coating compositions of the present invention maintain good corrosion resistance after at least 123 days of exposure.

Figures 3A, 3B:
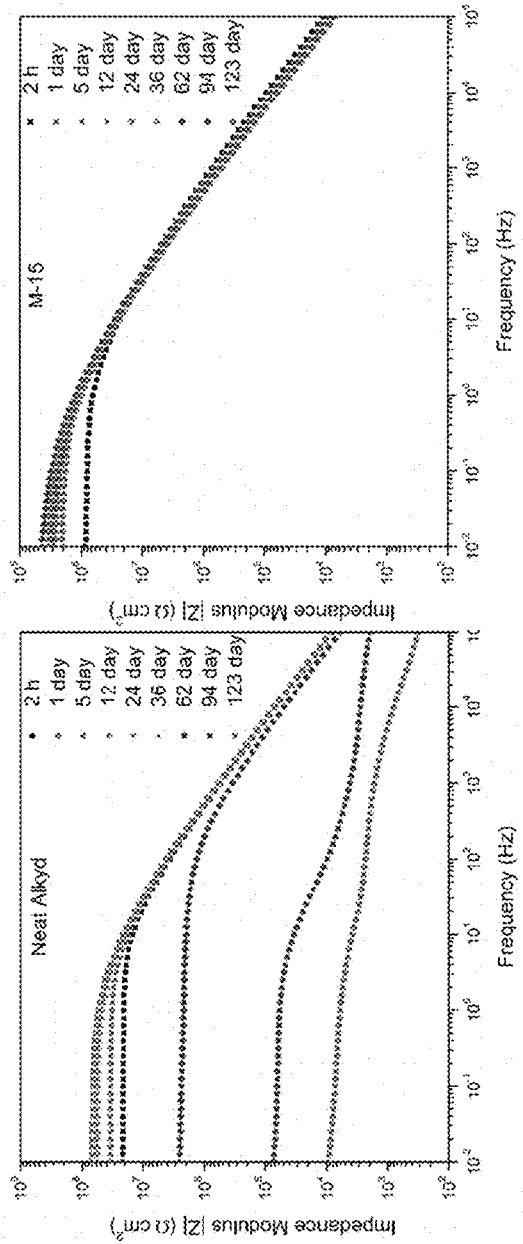
FIG. 3A shows Impedance modulus as a function of frequency for the neat alkyd coating.
FIG. 3B shows Impedance modulus as a function of frequency for the M-15 coating.

In one or more embodiments, the improvement in corrosion resistance coating compositions of the present invention may be demonstrated by immersing the coating in sodium chloride solution and evaluating the corrosion resistance of the coating by Electrochemical Impedance Spectroscopy (EIS). For example, as shown in FIG. 3, coating composition embodiments of the present invention exhibit an impedance modulus above $10^8$ ($\Omega$ $cm^2$) at low frequency during 123 days immersion.

In addition to coatings, the compositions of the present invention are useful as films, adhesives, and sealants.

In order to demonstrate the practice of the present invention, the following examples have been prepared and tested. The examples should not, however, be viewed as limiting the scope of the invention. The claims will serve to define the invention.

EXAMPLES

Synthesis of MACO.

Cardanol (30.0 g, 0.1 mol) methacrylic anhydride (18.5 g, 0.12 mol), and 4-deimethylaminopyridine (0.3 g, 2.4 mmol) were added into a flask equipped with a magnetic stirrer, a nitrogen gas inlet, and a nitrogen gas outlet. The reaction mixture was stirred at 45° C. under a nitrogen atmosphere. After 24 h, the reaction mixture was dissolved in dichloromethane and then washed with saturated sodium bicarbonate solution three times to remove the unreacted methacrylic anhydride and methacrylic acid. After that, the dichloromethane phase was further washed with 1.0 M NaOH solution, 1.0 M HCl solution, and deionized water. After washing, the organic phase was dried over anhydrous magnesium sulfate. After filtration, dichloromethane was removed by rotary evaporation to obtain MACO.

Synthesis of TSCO.

Cardanol (30.0 g, 0.1 mol), MEK (60.0 g, 0.8 mol), 3-isocyanatopropyl triethoxysilane (23.5 g, 95.0 mmol), and DBTDL (0.4 g, 0.6 mmol) were added into a flask equipped with a magnetic stirrer, a nitrogen gas inlet, and a nitrogen gas outlet. The reaction mixture was stirred at 65° C. under nitrogen atmosphere. After 12 h, MEK was removed by rotary evaporation to obtain TSCO.

Synthesis of Soybean Oil-Based Alkyd Resin.

The monoglyceride process was used to synthesize soybean oil-based alkyd, as shown in the Scheme 3 below. Soybean oil (200.0 g, 226.0 mmol) and glycerol (44.8 g, 486.5 mmol) were added into a flask equipped with a mechanical stirrer, a nitrogen gas inlet, a nitrogen gas outlet, a thermo couple and a reflux condenser. After the reactants were heated to 120° C., lithium hydroxide (38.3 mg 1.6 mmol) was added into the flask to catalyze the transesterification. The reaction mixture was further heated at 240° C. After 2 h, the reaction mixture was cooled to 100° C. and a Dean-Stark trap was installed on the reaction flask. Afterwards, phthalic anhydride (72.0 g, 486.1 mmol) and p-xylene (10.0 g, 94.2 mmol) were added into the reaction flask. Then, the temperature of the reactants was heated at 240° C. The reaction was stopped until the acid number of the reaction mixture was less than 10 mg KOH/g. The soybean oil-based alkyd resin was obtained as a brown viscous liquid.

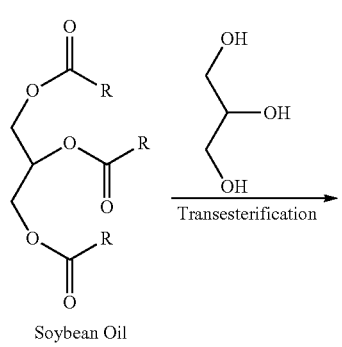

Scheme 3

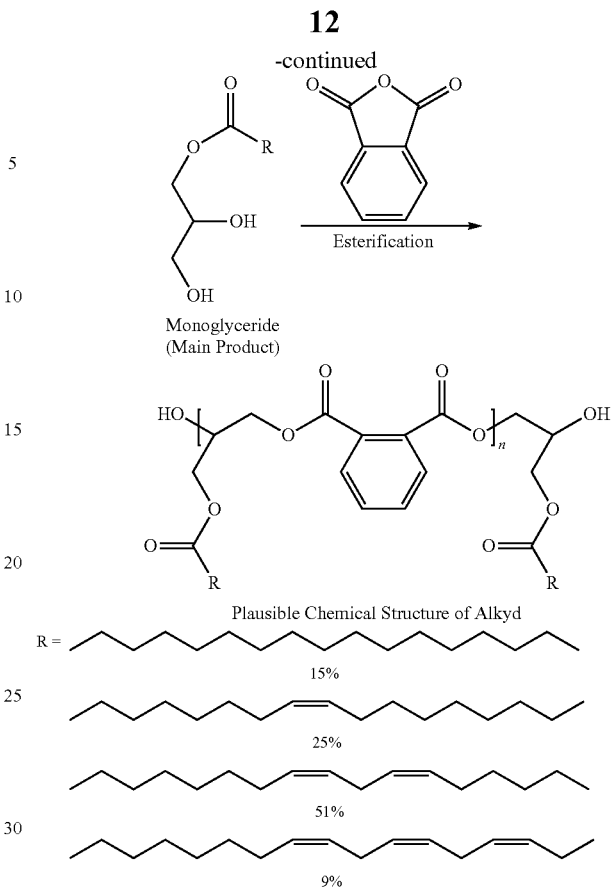

Coating Formulation and Preparation.

The cardanol-based reactive diluents (30 wt. %) were formulated with the soybean oil-based alkyd resin (68 wt. %) and drier package (2 wt. %) to prepare the coating films. The drier package includes 10 wt. % Cobalt Hydro-Cure II, 80 wt. % Zirconium Hydro-Cem, and 10 wt. % Calcium Hydro-Cem. The formulations containing cardanol, MACO, and TSCO were named as Alkyd-CO30, Alkyd-MACO30, and Alkyd-TSCO30, respectively. The neat alkyd coating was prepared by using 15 wt. % MEK as the diluent, 2 wt. % drier package, and 83 wt. % soybean oil-based alkyd resin. The coating samples were mixed well and cast onto clean steel panels (QD36, Q-Lab Corporation) and glass panels by a draw-down bar. The coatings on glass panels were used to make free films. The wet films were thermally cured at 120° C. for 2 h, followed by a second cure at 160° C. for 3 h. The thickness of all the cured coatings is in the range of 35-45 um.

Characterization of MACO and TSCO.

Figure 4:
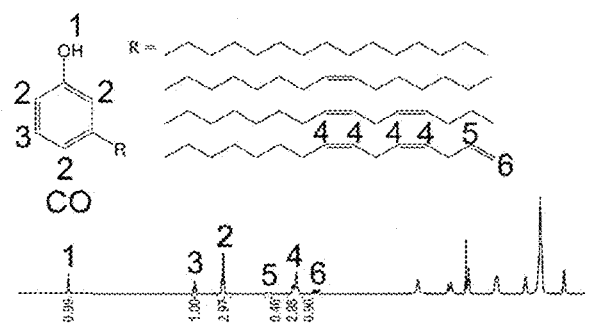
FIG. 4A is the $^1$H NMR spectra of cardanol (CO).
FIG. 4B is the $^1$H NMR spectra of MACO.
FIG. 4C is the $^1$H NMR spectra of TSCO.
Figure 4:
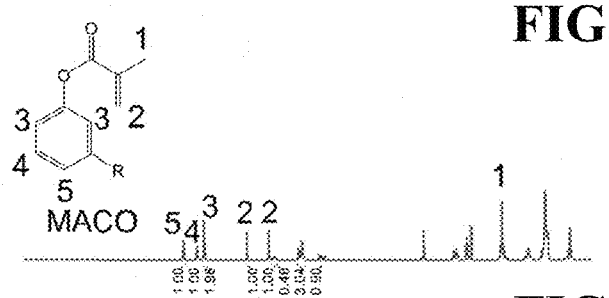
Figure 4:
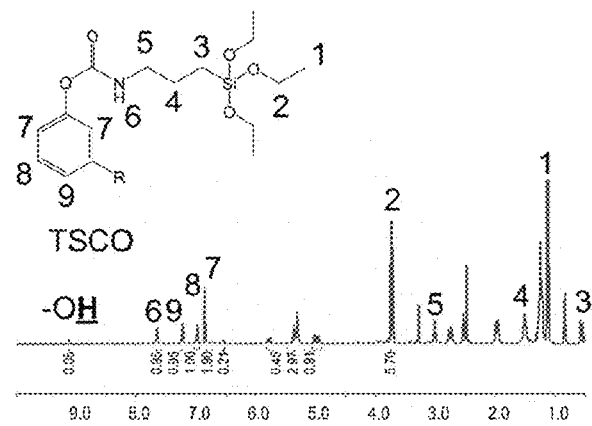
Figures 5A, 5B, 5C:
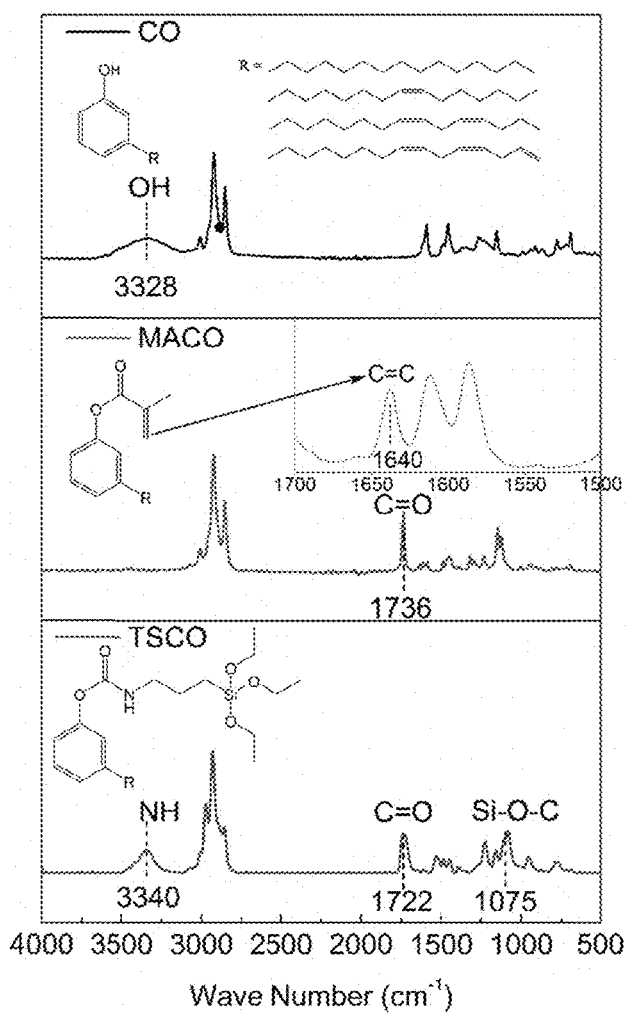
FIG. 5A is a FTIR spectra of CO.
FIG. 5B is a FTIR spectra of MACO.
FIG. 5C is a FTIR spectra of TSCO.

Fourier Transform Infrared Resonance (FTIR) and $^1$H NMR were used to characterize the synthesized MACO and TSCO. The successful esterification of cardanol with methacrylic anhydride can be confirmed by the disappearance of phenolic hydroxyl group and the occurrence of ester linkage. As shown in FIG. 4, the resonance at 9.15 ppm is assigned to the proton in the phenolic hydroxyl group of cardanol. In the $^1$H NMR spectra of MACO, the resonance at 9.15 ppm is disappeared, which indicates that almost all the phenolic hydroxyl groups have been reacted during the esterification. Moreover, the new absorption band at 1736 cm$^{-1}$ in the FTIR spectrum of MACO confirms the formation of carbonyl group in the ester linkage. See FIG. 5. Likewise, the successful urethanization of cardanol with 3-isocyanatopropyl triethoxysilane can be confirmed by the conversion of the phenolic hydroxyl group and the occurrence of urethane linkage. Considering the toxicity of the isocyanate group, the mole ratio of cardanol to 3-isocyanatopropyl triethoxysilane was set as 1 to 0.95 to ensure that all the isocyanate groups were reacted during synthesizing TSCO. On the basis of $^1$H NMR integration, the conversion of the phenolic hydroxyl group after urethanization is estimated to be 95%. In addition, there is no absorption band for the isocyanate group (2271 cm$^{-1}$) in the FTIR spectrum of TSCO, which indicates that all the isocyanate groups were reacted. Furthermore, the formation of urethane linkage can be confirmed by the new resonance in the $^1$H NMR spectra of TSCO and the new absorption band in the FTIR spectra of TSCO: the resonance at 7.67 ppm for the proton in the urethane linkage, the absorption band at 3340 cm$^{-1}$ for the amine group in the urethane linkage, and the absorption band at 1722 cm$^{-1}$ for carbonyl group in the urethane linkage. The evidence confirms that the modifications of cardanol are successful.

Diluent Efficiency.

Figure 6:
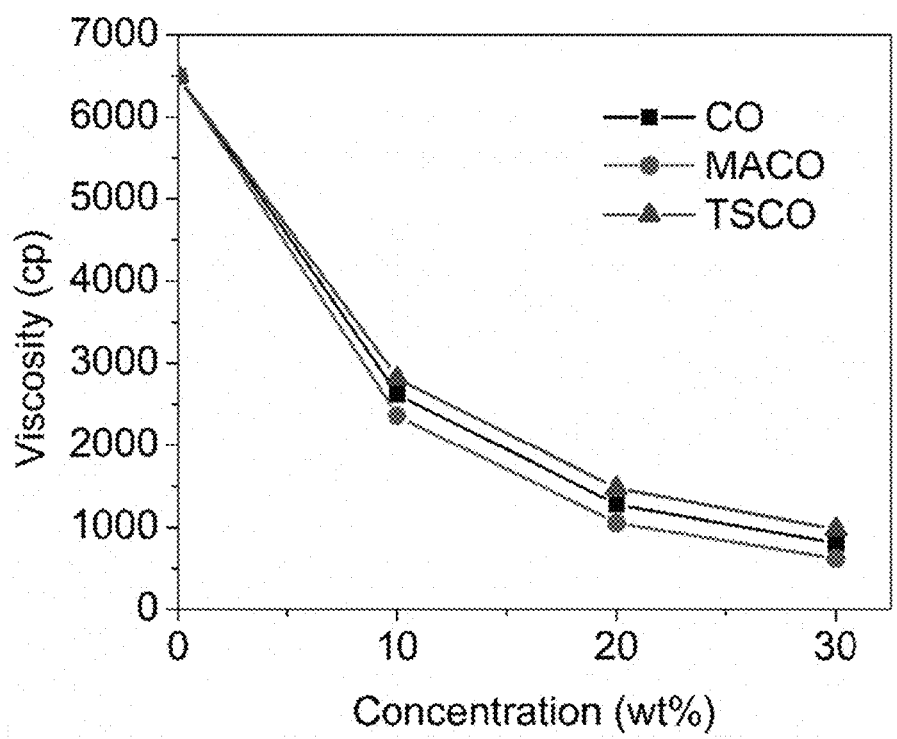
FIG. 6 shows viscosity of the soybean-oil based alkyd at different concentrations of the reactive diluents.

The diluent efficiency of cardanol-based reactive diluents was investigated by measuring the viscosity of the soybean oil-based alkyd system. FIG. 6 shows the viscosity change of the soybean oil-based alkyd system with increasing the concentration of cardanol-based reactive diluents. As expected, the viscosity of the soybean oil-based alkyd system shows a decreasing trend with increasing the concentration of cardanol-based reactive diluent. The viscosity of the neat soybean oil-based alkyd is 6500 cp. For the soybean oil-based alkyd systems containing 30 wt. % of CO-based reactive diluents, the viscosity was reduced to 815 cp for Cardanol, 625 cp for MACO, and 980 cp for TSCO. The diluent efficiency can be quantified by the reduction of viscosity, when compared to the same composition but without the reactive diluent. Taking the soybean oil-based alkyd systems containing 30 wt. % cardanol-based reactive diluents as the examples, MACO shows higher diluent efficiency (90.4%) among cardanol (87.5%) and TSCO (84.9%). All of them showed excellent dilution efficiency for the soybean oil-based alkyd.

Coating Properties.

The coatings containing 30 wt. % cardanol, MACO, and TSCO were named as Alkyd-CO30, Alkyd-MACO30, and Alkyd-TSCO30, respectively. The coating properties are summarized in Table 1 and Table 2. In general, the coating performances are increased by using TSCO as the reactive diluent.

TABLE 1

Gel content and viscoelastic properties of prepared alkyd coatings.

| | Gel Content (wt. %) | $T_g$ (° C.) | E' at $T_g$ + 50 ° C. (MPa) | $\square_e$ (mol/m$^3$) |
|---|---|---|---|---|
| Neat Alkyd | 87.37 | 47.23 | 0.83 | 89.85 |
| Alkyd-CO30 | 73.52 | 29.73 | 0.26 | 29.54 |
| Alkyd-MACO30 | 85.86 | 39.29 | 0.63 | 69.69 |
| Alkyd-TSCO30 | 92.31 | 60.98 | 3.81 | 397.66 |

(Alkyd-CO30: the alkyd coating formulated with 30 wt. % Cardanol;
Alkyd-MACO30: the alkyd coating formulated with 30 wt. % MACO;
Alkyd-TSCO30: the alkyd coating formulated with 30 wt. % TSCO;
$T_g$: Glass transition temperature;
E': Storage modulus;
$\square_e$: Cross-link density.)

TABLE 2

Adhesion, mechanical properties, and solvent resistance of the alkyd coatings.

| | Neat Alkyd | Alkyd-CO30 | Alkyd-MACO30 | Alkyd-TSCO30 |
|---|---|---|---|---|
| Crosshatch Adhesion | 5B | 5B | 5B | 5B |
| Tensile Modulus [MPa] | 6.73 ± 1.21 | 1.87 ± 0.32 | 4.30 ± 0.75 | 38.21 ± 5.33 |
| Tensile Strength [MPa] | 3.74 ± 0.92 | 0.97 ± 0.21 | 2.63 ± 0.42 | 10.53 ± 2.38 |
| Elongation at break [%] | 75.52 ± 10.37 | 59.43 ± 9.33 | 71.73 ± 15.22 | 42.67 ± 7.87 |
| Pencil Hardness | 3H | F | 2H | 6H |
| Mandrel Bend Flexibility | >32% | >32% | >32% | >32% |
| MEK Double Rubs | 115 | 15 | 78 | 190 |

(Alkyd-CO30: the alkyd coating formulated with 30 wt. % Cardanol;
Alkyd-MACO30: the alkyd coating formulated with 30 wt. % MACO;
Alkyd-TSCO: the alkyd coating formulated with 30 wt. % TSCO.)

Material for the Following Experiments.

Xylene (Certified ACS) was purchased from Fisher scientific. Zinc phosphate (ZP 10) was supplied by Heubach (PA, US). Cobalt Hydro-Cure II, Zirconium Hydro-Cem, and Calcium Hydro-Cem were supplied by OMG Group (OH, US). MACO and TSCO were synthesized according to the procedures described above.

Synthesis of Linseed Oil-Based Alkyd Resin.

A linseed oil-based alkyd resin was synthesized according to the procedure described above for the soybean oil-based alkyd resin, utilizing the ingredients and amounts that are summarized in Table 3.

TABLE 3

| Linseed Oil | Glycerol | Phthalic Anhydride | Lithium Hydroxide |
|---|---|---|---|
| 100 g | 26.5 g | 47.1 g | 0.18 g |

The linseed oil alkyd resin may be represented by the following chemical structure:

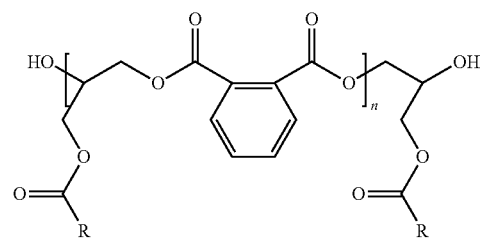

-continued

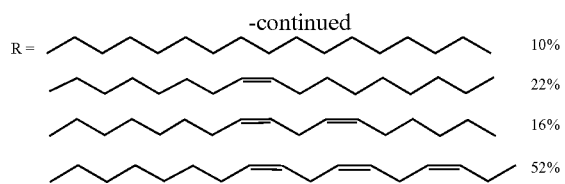

| R = | | |
|---|---|---|
| | | 10% |
| | | 22% |
| | | 16% |
| | | 52% |

In other words, the linseed oil alkyd resin was determined to be a mixture of compounds having the above structure, where R varied as shown.

Coating Formulations and Preparation.

The formulations of the zinc phosphate pigmented alkyd coatings are shown in Table 4.

TABLE 4

Zinc phosphate pigmented alkyd coating formulations.

| | Neat Alkyd | M-5 | M-10 | M-15 | T-5 | T-10 | T-15 |
|---|---|---|---|---|---|---|---|
| Xylene (wt. %) | 20 | 17 | 14 | 11 | 17 | 14 | 11 |
| MACO (wt. %) | 0 | 5 | 10 | 15 | 0 | 0 | 0 |
| TSCO (wt. %) | 0 | 0 | 0 | 0 | 5 | 10 | 15 |
| Alkyd (wt. %) | 36 | 32 | 29 | 25 | 32 | 29 | 25 |
| Zinc Phosphate (wt. %) | 42 | 44 | 45 | 47 | 44 | 45 | 47 |
| Drier (wt. %) | 2 | 2 | 2 | 2 | 2 | 2 | 2 |
| Total (wt. %) | 100 | 100 | 100 | 100 | 100 | 100 | 100 |
| Solid Content (wt. %) | 80 | 83 | 86 | 89 | 83 | 86 | 89 |
| Viscosity (cp) | 323 | 317 | 324 | 331 | 326 | 340 | 342 |

Neat alkyd represents the alkyd coating without MACO and TSCO. M-5, M-10, and M-15 represent the alkyd coatings containing 5 wt. %, 10 wt. %, and 15 wt. % MACO, respectively. T-5, T-10, and T-15 represent the alkyd coatings containing 5 wt. %, 10 wt. %, and 15 wt. % TSCO, respectively. The pigment volume concentration (PVC) were kept as 29% for all the coating formulations. 2 wt. % drier package (10 wt. % Cobalt Hydro-Cure II, 80 wt. % Zirconium Hydro-Cem, and 10 wt. % Calcium Hydro-Cem) was added into each formulation to catalyze the oxidative cross-linking reaction. From Table 4, it was found that 5 wt. % of MACO or TSCO can reduce the usage of xylene by 3 wt. % while the coating systems still have a similar viscosity. The zinc phosphate pigment was dispersed by a homogenizer (SCILOGEX D-160) at 10000 rpm in an ice bath for 0.5 h. The fineness of the dispersed zinc phosphate was less than 10 um which was tested according to ASTM D1210. The coatings were applied on steel substrates (Q-Lab Corporation, QD-36) by a drawdown bar, and kept in a dust-free chamber for 30 days at room temperature before any tests were performed. The dry film thickness of all the coating samples was in the range of 50-60 um.

Coating Characterization

The viscosity of the liquid coatings was tested by a rotating viscometer (BYK) at 10 rpm. ASTM standards were used to characterize the drying time (D5895), pull-off adhesion (D4541), and salt spray resistance (B117) of the prepared coatings. EIS measurements were conducted by a Reference 600 potentiostat (Gamry Instruments). The prepared coatings were immersed in 3.5 wt. % NaCl solution with an exposure area of 7 cm². The typical three-electrode cell was used which consists of a reference electrode (saturated calomel), a counter electrode (platinum mesh), and a working electrode (coated steel). All the measurements were carried out at room temperature using a frequency range of 100 kHz to 10 mHz with 10 mV (versus open circuit potential) AC perturbation. Equivalent circuit modeling of the EIS spectra was operated on the Gamry Echem Analyst software.

Generally a coating that dries within several hours is desirable because a long drying time limits the outdoor application of a coating. The drying process refers to the transition process of a liquid coating to a solid film, which is also called film formation process and curing process. As shown in Table 5, compared with the neat alkyd coating, the drying time of the alkyd coatings containing 10 wt. % and 15 wt. % TSCO was increased to 16 h and 24 h, respectively. Without wishing to be bound by theory, it may be that the longer drying time is due to the low reactivity of the ethoxysilane group at room temperature, which may result in a longer induction time to generate the siloxane network.

TABLE 5

Drying time and pull-off adhesion of the prepared alkyd coatings.

| | | Pull-Off Adhesion | |
|---|---|---|---|
| | Dry-Through Time (h) | Strength (psi) | Failure Type |
| Neat Alkyd | 12 | 251 ± 17 | Mix[a] |
| M-5 | 12 | 256 ± 12 | Mix |
| M-10 | 8 | 292 ± 16 | Mix |
| M-15 | 8 | 304 ± 19 | Mix |
| T-5 | 12 | 246 ± 11 | Mix |
| T-10 | 16 | 217 ± 13 | Mix |
| T-15 | 24 | 197 ± 10 | Mix |

[a]The mix of cohesive failure and adhesive failure

The drying time of the alkyd coatings containing 10 wt. % and 15 wt. % MACO was 4 h shorter than that of the neat alkyd coating. Without wishing to be bound by theory, it may be that the shorter drying time is because MACO can contribute in the drying process of the bottom layer alkyd coating. One criteria for drying for a coating is the capability to resist mechanical deformation under a certain pressure. It is known that the drying process of an alkyd is affected by the oxidative cross-linking. The oxidative cross-linking of an alkyd is dependent on the oxygen in air; and may be governed by the diffusion of oxygen into the coating film. For the surface layer of an alkyd coating, the drying is typically much faster than the lower layer and as a consequence, the cross-linked surface layer retards the diffusion of oxygen into the depth of the alkyd coating. Therefore, the diffusion of oxygen into the alkyd coating is often the rate-limiting step in the drying process.

In the present invention, the decreased drying time of M-10 and M-15 is surprising, and may be due to homopolymerization of MACO, which may help build the mechanical strength of the bottom coating layer. As illustrated in FIG. 1, the remaining methacrylate moieties in the lightly cross-linked bottom layer can undergo a free radical homo-polymerization. The hydroperoxides generated from the autoxidation process can be considered as free radical initiators to induce the homo-polymerization. The homo-polymerization can increase the cross-linking density and mechanical strength of the bottom layer, and thereby decrease the drying time.

Pull-Off Adhesion

Adhesion is often an important property for a coating. Table 5 presents the pull-off adhesion strength and failure type of the prepared alkyd coatings. The failure type of all the alkyd coatings is the mix of adhesive failure and cohesive failure, which indicates that the mechanical strength of the alkyd coatings plays a considerable influence on the pull-off adhesion strength. Similar to the drying time, the pull-off adhesion strength of the TSCO alkyd coating was decreased with the increase of TSCO. This can be attributed to the low reactivity of the ethoxysilane groups at room temperature. For the alkyd coatings containing 10 wt. % and 15 wt. % MACO, the pull-adhesion strength was higher than the neat alkyd coating by around 50 psi. The improved pull-off adhesion strength may result from the increased mechanical strength of the alkyd coatings; and the enhanced mechanical strength can be attributed to the homo-polymerization of the methacrylate moieties, as discussed above. Because the highly cross-linked surface layer retards the diffusion of oxygen into the bottom layer, the oxidative cross-linking of alkyd is not homogeneous across the depth of the coating; as a result, the mechanical strength is inhomogeneous; and the bottom layer is much weaker than the surface layer for a room temperature cured alkyd coating. The addition of MACO provides another cross-linking reaction (homo-polymerization of the methacrylate moieties) that can occur in the absence of oxygen. Similar to decrease the drying time, the additional cross-linking by MACO increases the cross-link density of the bottom layer. Therefore, the overall mechanical strength and pull-off adhesion strength of the alkyd coating is improved by MACO.

Corrosion Resistance: Salt Spray

The corrosion resistance of the prepared alkyd coatings was evaluated via salt spray test (ASTM B117). FIG. 2 shows the appearance of the alkyd coatings after 480 h exposure in a salt fog chamber. Serious corrosion was observed for the neat alkyd coating, the alkyd coatings containing TSCO, and the alkyd coating containing 5 wt. % and 10 wt. % MACO. Although a few blisters were found on M-15, its appearance was much better than other alkyd coatings. The results of salt spray test indicate that the addition of 15 wt. % MACO into the formulation can significantly improve the corrosion resistance of the zinc phosphate pigmented alkyd coating.

Corrosion Resistance: EIS

In order to further demonstrate the improvement of corrosion resistance for the zinc phosphate pigmented alkyd coating, M-15 and the neat alkyd coating were immersed in the 3.5 wt. % NaCl aqueous solution and characterized by EIS. EIS has been demonstrated as a powerful method to evaluate the corrosion resistance of polymeric coatings. Several physical parameters that are corresponding to the corrosion resistance of coatings can be obtained from EIS. FIG. 3 presents the impedance modulus (|Z|) of the neat alkyd coating and M-15 as a function of frequency and the immersion time. The impedance modulus has a significant decrease of the neat alkyd coating under 123 days' immersion; however, the impedance modulus of M-15 kept above $10^8$ ($\Omega$ cm2) at low frequency during the immersion. This obvious difference clearly demonstrates that 15 wt. % MACO modification has significantly improved the corrosion resistance of the alkyd coating.

Previous studies suggest that the |Z| at low frequency region can serve as the parameter to evaluate the corrosion resistance of a polymeric coating since it usually represents the resistance of the coating system. In order to clearly compare the difference between the neat alkyd coating and M-15, the |Z| at the low frequency (0.01 Hz) as a function of immersion time is plotted and shown in FIG. 7. During the first 5 days of immersion, the |Z| at 0.01 Hz shows an obvious increase for both the neat alkyd coating and M-15. This can be related to the inhibitive effect of zinc phosphate pigments. During the 36 days to 123 days immersion period, a remarkable decrease of the |Z| at 0.01 Hz is found for the neat alkyd coating which demonstrates a serious coating degradation, while the |Z| at 0.01 Hz for M-15 presents a stable trend throughout the immersion period. This result further demonstrates that the corrosion resistance of M-15 is much better than the neat alkyd coating.

Equivalent Circuit Modeling

Figure 8:
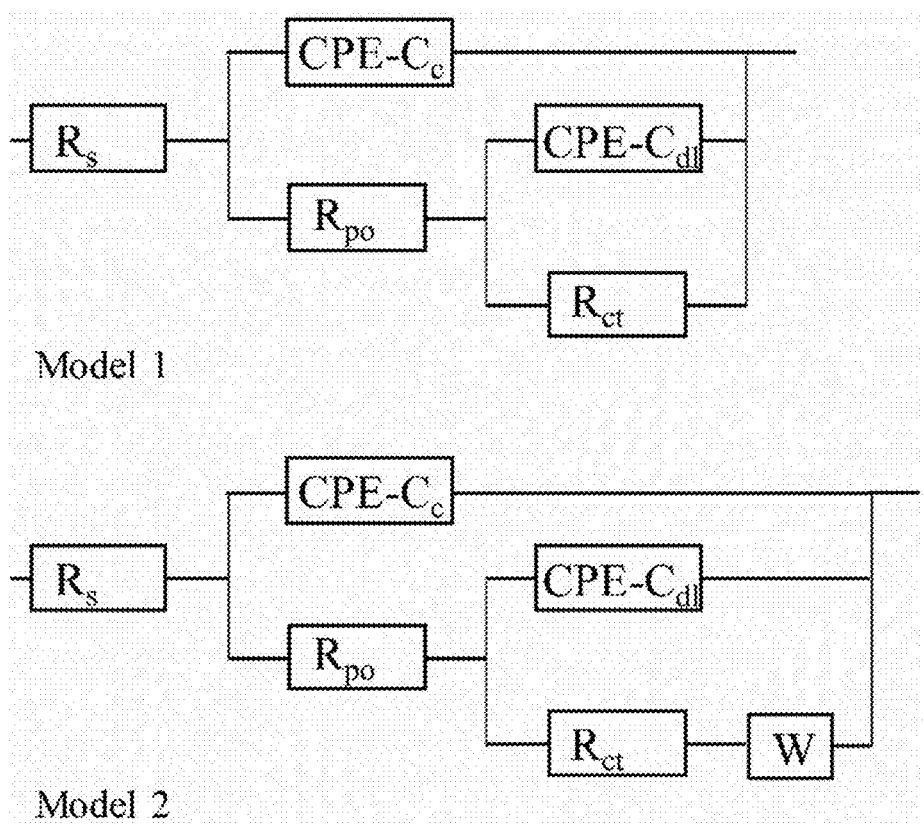
FIG. 8 illustrates equivalent circuit models used for alkyd coatings in this invention.
Figures 9A, 9B:
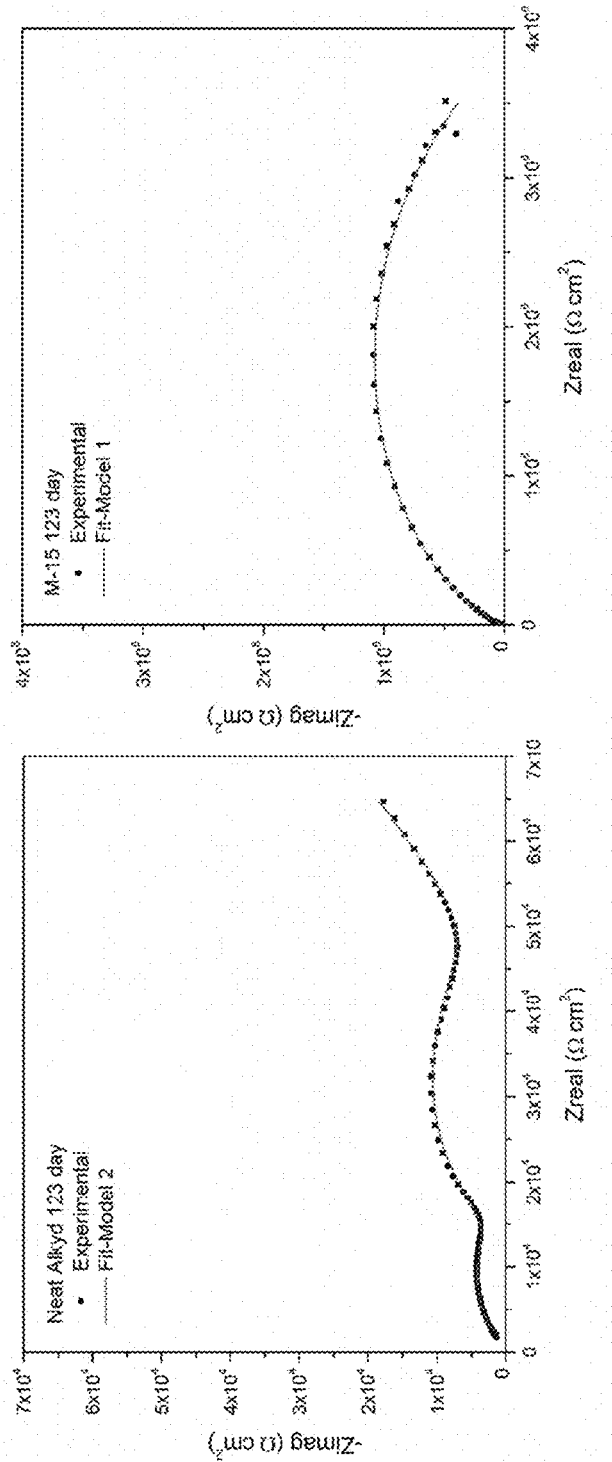
FIG. 9A shows the representative Nyquist plots and the corresponding fit curves of the neat alkyd coating after 123 days of immersion.
FIG. 9B shows the representative Nyquist plots and the corresponding fit curves of the M-15 after 123 days of immersion.

In order to analyze the physical behavior of the coating samples, equivalent circuit modeling is employed in this invention. FIG. 8 presents the equivalent circuit models used for the alkyd coatings. Model 1 has been widely used to fit the polymer coatings in a corrosive electrolyte due to the good corresponding of the electrical elements with the physical meanings of the coating system. In this model, $R_s$ represents the solution resistance; $R_{po}$ is the coating pore resistance; $C_c$ is the coating capacitance; $R_{ct}$ is the charge transfer resistance of electrochemical corrosion process; and $C_{dl}$ is double layer capacitance. Constant phase elements (CPE) is used to replace the capacitance element due to the non-ideal capacitance behavior of the coating system. $R_{po}$ in parallel with $C_c$ represents the bulk coating properties; and $R_{ct}$ in parallel with $C_{dl}$ is used to characterize the coating-metal interface. Model 2 is the modified version of Model 1 in which one Warburg diffusion element (W) is introduced in series with $R_{ct}$. The occurrence of the Warburg diffusion is attributed to the presence of corrosion products on the electrochemically active site. FIG. 9 shows the representative Nyquist plots and the corresponding fit curves of the neat alkyd coating and MACO-15 after 123 days of immersion. Model 1 was used to fit the data of MACO-15; and Model 2 was used to fit the data of the neat alkyd coating because the diffusion tail was found on its Nyquist plot.

Figure 7:
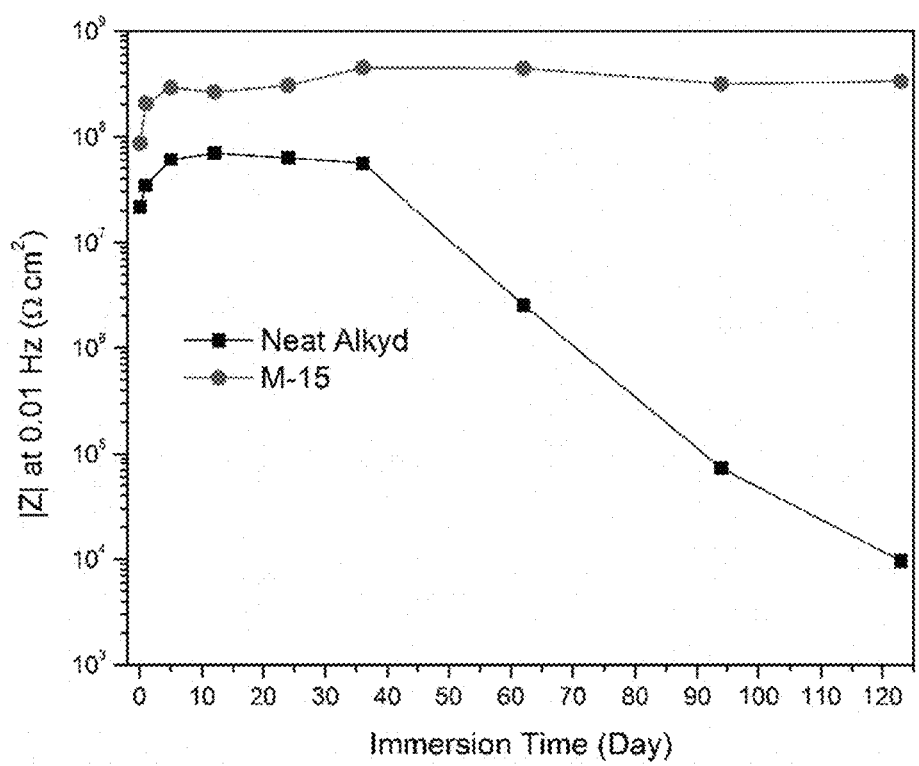
FIG. 7 shows impedance modulus (|Z|) at 0.01 Hz as a function of immersion time for neat alkyd coating and M-15.
Figures 10A, 10B:
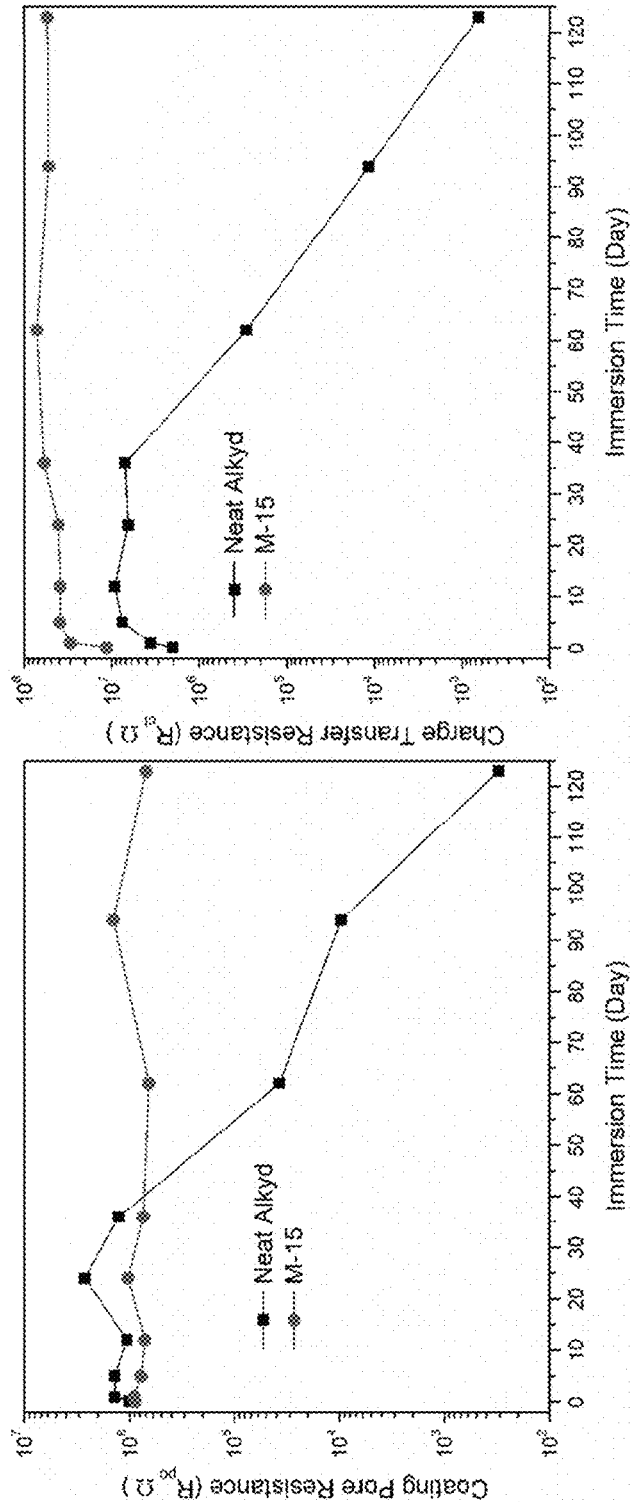
FIG. 10A shows coating pore resistance ($R_{po}$) as a function of immersion time for neat alkyd coating and M-15.
FIG. 10B shows coating charge transfer resistance ($R_{ct}$) as a function of immersion time for neat alkyd coating and M-15.

The evolution of $R_{po}$ and $R_{ct}$ for the coating samples was presented at FIG. 10 to assess the status of the bulk coatings and the coating-metal interfaces, respectively. An increase of $R_{ct}$ was found for both the neat alkyd coating and the M-15 during the first 5 days of immersion, which is consistent with the low frequency EIS data (FIG. 7). This can be attributed to the formation of passive layers at the coating-metal interface from the zinc phosphate pigments. The $R_{ct}$ and $R_{po}$ of M-15 were maintained at above $10^7\Omega$ and around $10^6\Omega$, respectively, during the 123 days of immersion, which indicates that there was no significant degradation on the coating sample of M-15.

Figure 11:
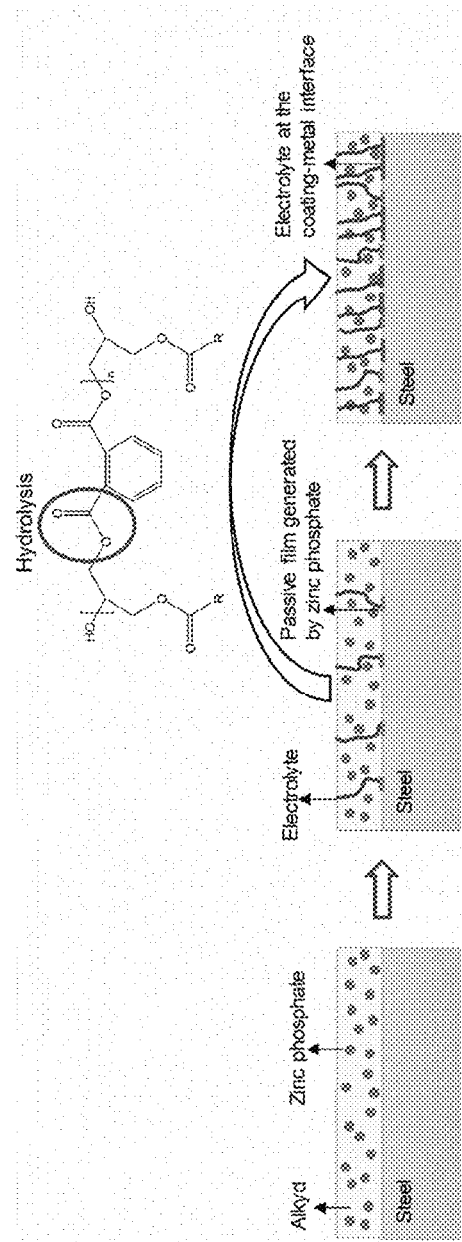
FIG. 11 shows the proposed degradation process of the neat alkyd coating.

On the basis of the change in $R_{po}$ and $R_{ct}$, a degradation process for the neat alkyd coating is proposed and presented in FIG. 11. For the neat alkyd coating, the $R_{po}$ showed a decreasing trend after 36 days of immersion and dropped to $\sim 10^2\Omega$ after 123 days of immersion. This suggests that the neat alkyd coating was becoming more permeable to the electrolyte during the immersion. During the 36 to 123 days of immersion period, the $R_{ct}$ of the neat alkyd coating also presented a decreasing trend, which could be corresponded to the delamination of the coating and the accumulation of electrolyte at the coating-steel interface. One reason for the increase of the permeability to the electrolyte is the hydrolysis of the ester bonds in the backbone of the alkyd; as a result, the continuity of the coating system is broken. The loss of continuity further leads to the severe penetration of electrolyte and the coating delamination.

As evidenced by the salt spray and EIS test, M-15 presented superior corrosion resistance to the neat alkyd coating. One explanation for the improved corrosion resistance is that the addition of 15 wt. % MACO greatly improves the hydrolytic resistance of the alkyd coating system. The backbone of the homo-polymers of MACO is held by carbon-carbon bonds, which is hydrolysis resistant. In the formulation of M-15, the weight ratio of MACO to alkyd resin is 3 to 5, which means that MACO is a vital part in building the continuous binder phase of the coating system. Due to the presence of significant amount of MACO, the coating sample of M-15 maintains the continuity and barrier property throughout the 123 days of immersion.

It has been shown herein that, in one or more embodiments, the cardanol-based reactive diluents of the present invention are useful for alkyd coating applications. In one or more embodiments, the viscosity of the alkyd resin is significantly reduced by using the cardanol-based reactive diluents (e.g., over 84% diluent efficiency at 30 wt. % loading). The modified cardanol reactive diluents exhibit the ability to participate in the cross-linked network of the alkyd. Moreover, in one or more embodiments, the cross-link density of the alkyd coating is significantly improved by using the modified cardanol reactive diluent, and the mechanical strength and solvent resistance of the alkyd coating is improved.

In one or more embodiments, the reactive diluents of the present invention increase the corrosion resistance and solid content of a conventional solvent borne zinc phosphate pigmented alkyd coating. The presence of about 5 wt. % of MACO or TSCO can reduce the dosage of xylene by about 3 wt. % while maintaining the viscosity of the alkyd coating system. In some embodiments, TSCO presented a negative influence on the drying time and the pull-off adhesion strength of the alkyd coating; however, the addition of 10 wt. % or 15 wt. % MACO decreased the drying time from 12 h to 8 h and increased the pull-off adhesion strength from ~250 psi to ~300 psi, comparing with the neat alkyd coating (without MACO and TSCO). As evidenced by the salt spray test, the addition of TSCO did not show an enhancement of corrosion resistance for the alkyd coating; however, the alkyd coating containing 15 wt. % MACO (labelled as M-15) presented superior corrosion resistance to other coating systems. M-15 and the neat alkyd coating were further characterized by EIS. The results of EIS further demonstrated that the corrosion resistance of M-15 is much better than the neat alkyd coating in the 3.5 wt. % NaCl solution immersion. Importantly, M-15 can provide an excellent protection of the steel in the corrosive immersion condition for at least 123 days. The improvement of the overall performance was attributed to the homo-polymerization of the methacrylate moiety in MACO. In conclusion, using MACO as the reactive diluent enables formulating environmentally friendly high solid alkyd coatings with excellent corrosion resistance.

Advantageously, the addition of 15 wt. % MACO into a zinc phosphate pigmented alkyd coating system can reduce the usage of organic solvent, decrease the drying time, increase the pull-off adhesion strength, and improve the corrosion resistance. The alkyd coating containing 15 wt. % MACO showed exceptional corrosion resistance in the immersion condition for over 123 days. The improvement of the overall performance was attributed to the homo-polymerization of the methacrylate moiety in MACO.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. An alkyd coating composition comprising:
    at least one alkyd resin;
    at least one reactive diluent selected from modified cardanol and represented by the following formula:

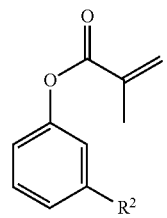

wherein $R^2$ is a $C_{15}$ hydrocarbon chain containing from zero to three double bonds;
optionally, at least one dryer agent;
optionally, at least one pigment;
optionally, at least one solvent; and
wherein the alkyd coating composition includes a solids content of 70% or greater by weight of all ingredients other than any solvent present by total weight of the alkyd coating composition.

2. The composition of claim 1, wherein the at least one reactive diluent includes the following distribution for $R^2$:

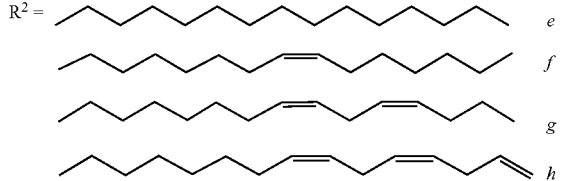

wherein e, f, g and h are individually percentages of from 0 to about 100, based upon the total weight of the modified cardanol, and wherein e+f+g+h=100.

3. The composition of claim 1, wherein the coating composition includes from about 1 to about 40 wt. % reactive diluent, based upon the total weight of the composition.

4. The composition of claim 1, wherein a volatile organic content (VOC) of the composition is 300 g/l or less, as determined in accordance with US standard ASTM D 2369 for one hour at 110° C.

5. The composition of claim 1, wherein an air drying time of a wet film cast from the composition is reduced by 4 hours when compared to a composition without the reactive diluent.

6. The composition of claim 1, wherein the composition is devoid of any organic solvent.

7. A method for forming an alkyd coating for corrosion protection on a substrate, the method comprising:
providing a substrate suitable for being coated;
providing a coating composition that comprises
at least one alkyd resin;
at least one reactive diluent selected from modified cardanol and represented by the following formula:

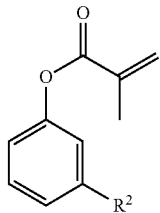

wherein $R^2$ is a $C_{15}$ hydrocarbon chain containing from zero to three double bonds;
optionally, at least one corrosion-inhibitive pigment;
optionally, at least one dryer agent;
optionally, at least one solvent; and
wherein the coating composition includes a solids content of 70% or greater by weight of all ingredients other than any solvent present by total weight of the coating composition;
casting the coating composition on the substrate to thereby form a wet film on the substrate;
curing the wet film to thereby form the alkyd coating on the substrate.

8. The method for forming an alkyd coating according to claim 7, wherein the coating composition is curable at room temperature or is thermally cured.

9. The method for forming an alkyd coating according to claim 7, wherein the at least one reactive diluent includes the following distribution for $R^2$:

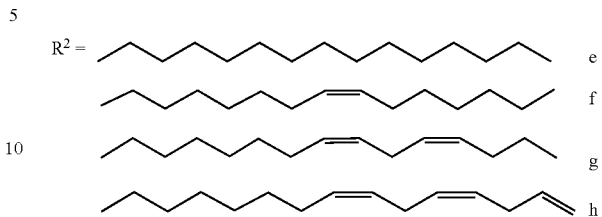

wherein e, f, g and h are individually percentages of from 0 to about 100, based upon the total weight of the modified cardanol, and wherein e+f+g+h=100.

10. The method for forming an alkyd coating according to claim 7, wherein a volatile organic content (VOC) of the composition is 300 g/l or less, as determined in accordance with US standard ASTM D 2369 for one hour at 110° C.

11. The method for forming an alkyd coating according to claim 7, wherein the step of curing the wet film includes air drying the wet film, and wherein an air drying time of the wet film cast from the coating composition is reduced by 4 hours or more when compared to a composition without the reactive diluent.

12. The method for forming an alkyd coating according to claim 7, wherein the coating composition is devoid of any organic solvent.

13. The method for forming an alkyd coating according to claim 7, wherein the coating composition includes at least one corrosion-inhibitive pigment, and wherein the substrate comprises steel.

* * * * *